(12) United States Patent
Higuchi

(10) Patent No.: US 9,055,903 B2
(45) Date of Patent: Jun. 16, 2015

(54) FUNDUS PHOTOGRAPHING APPARATUS

(71) Applicant: NIDEK CO., LTD., Gamagori-shi, Aichi (JP)

(72) Inventor: Yukihiro Higuchi, Gamagori (JP)

(73) Assignee: NIDEK CO., LTD., Aichi (JP)

( * ) Notice: Subject to any disclaimer, the term of this patent is extended or adjusted under 35 U.S.C. 154(b) by 9 days.

(21) Appl. No.: 13/827,821

(22) Filed: Mar. 14, 2013

(65) Prior Publication Data
US 2013/0265547 A1    Oct. 10, 2013

(30) Foreign Application Priority Data

Mar. 30, 2012   (JP) ................................. 2012-080997

(51) Int. Cl.
| | |
|---|---|
| *A61B 3/14* | (2006.01) |
| *A61B 3/00* | (2006.01) |
| *A61B 3/10* | (2006.01) |
| *A61B 3/15* | (2006.01) |
| *G01B 9/02* | (2006.01) |
| *A61B 5/00* | (2006.01) |

(52) U.S. Cl.
CPC ................. *A61B 3/152* (2013.01); *A61B 3/102* (2013.01); *A61B 5/0066* (2013.01); *G01B 9/02091* (2013.01); *G01B 9/02203* (2013.01); *G01B 9/02063* (2013.01); *G01B 9/02068* (2013.01)

(58) Field of Classification Search
CPC .......... A61B 3/103; A61B 3/14; A61B 3/113; A61B 3/152; A61B 3/1015; A61B 3/1225
USPC .......... 351/205–206, 210, 221, 200, 246, 208
See application file for complete search history.

(56) References Cited

U.S. PATENT DOCUMENTS

| | | |
|---|---|---|
| 2008/0002151 A1 | 1/2008 | Hideshima et al. |
| 2008/0100612 A1 | 5/2008 | Dastmalchi et al. |
| 2009/0180073 A1 | 7/2009 | Ichikawa et al. |
| 2009/0303438 A1 | 12/2009 | Yamada et al. |
| 2010/0182567 A1 | 7/2010 | Nouchi et al. |
| 2011/0176111 A1* | 7/2011 | Taki et al. ..................... 351/207 |

(Continued)

FOREIGN PATENT DOCUMENTS

JP         2009-291252 A     12/2009

OTHER PUBLICATIONS

Extended European Search Report issued Jul. 24, 2013, corresponds to EP13159341.0.

*Primary Examiner* — Dawayne A Pinkney
(74) *Attorney, Agent, or Firm* — Rankin, Hill & Clark LLP

(57) ABSTRACT

A fundus photographing apparatus includes a measurement unit including an optical coherence tomography system for obtaining a tomographic image of the fundus of an examinee's eye by detecting an interference state between measurement light from the fundus of the examinee's eye and reference light, a detection unit for detecting an alignment state perceived as a relative positional relationship between the measurement unit and the examinee's eye, and a controller for adjusting the optical coherence tomography system with respect to the fundus of the examinee's eye based on a detection result from the detection unit. The adjustment of the optical coherence tomography system includes at least one of an optical path length adjustment, which adjusts an optical path length difference between the measurement light and the reference light, and a focus adjustment.

20 Claims, 4 Drawing Sheets

(56) References Cited

U.S. PATENT DOCUMENTS

2011/0267583 A1* 11/2011 Hayashi .................. 351/206
2011/0286003 A1    11/2011 Ono
2012/0249961 A1* 10/2012 Muto ...................... 351/208
2013/0222566 A1*  8/2013 Murase ..................... 348/78

* cited by examiner

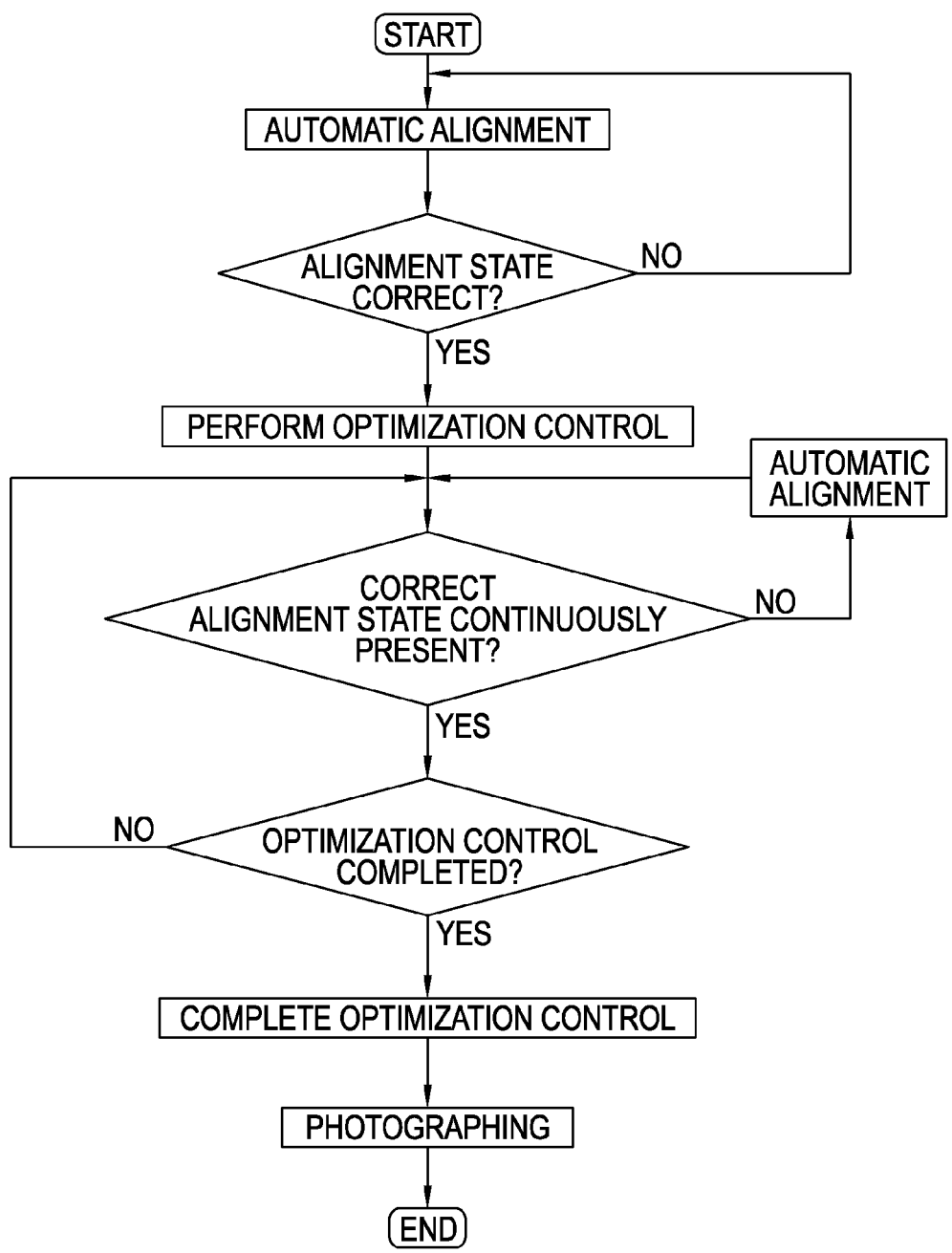

FUNDUS PHOTOGRAPHING APPARATUS

CROSS-REFERENCE TO RELATED APPLICATION

This application is based on Japanese Patent Application No. 2012-080997 filed with the Japan Patent Office on Mar. 30, 2012, the entire content of which is hereby incorporated by reference.

BACKGROUND

1. Technical Field

The present disclosure relates to a fundus photographing apparatus that captures a tomographic image of the fundus of an examinee's eye.

2. Related Art

As a fundus photographing apparatus that captures a tomographic image of the fundus of an examinee's eye, optical coherence tomography (OCT) which uses low coherence light is known (see JP 2009-291252 A).

When such a device is used, the examiner adjusts the positional relationship (alignment state) between the examinee's eye and the device body by using an operating member, such as a joystick, prior to conducting photography. Then, the examiner presses a button on the device for starting optimization control, and the device starts photographing condition optimization control (optical path length adjustment, focus adjustment and/or polarization state adjustment (polarizer adjustment).

SUMMARY

A fundus photographing apparatus includes: a measurement unit including an optical coherence tomography system configured to obtain a tomographic image of the fundus of an examinee's eye by detecting an interference state between measurement light from the fundus of the examinee's eye and reference light; a detection unit configured to detect an alignment state perceived as a relative positional relationship between the measurement unit and the examinee's eye; and a controller configured to perform adjustment of the optical coherence tomography system with respect to the fundus of the examinee's eye based on a detection result from the detection unit. The adjustment of the optical coherence tomography system includes at least one of an optical path length adjustment, which adjusts an optical path length difference between the measurement light and the reference light, and a focus adjustment.

BRIEF DESCRIPTION OF DRAWINGS

FIG. 3 is a flowchart illustrating the flow of a control operation according to the example.

DETAILED DESCRIPTION

Figure 1:
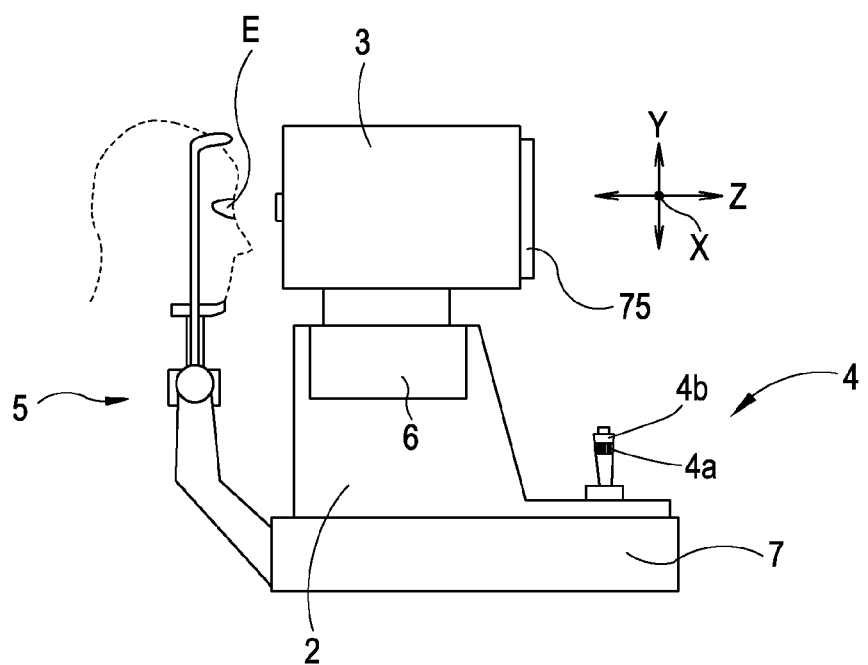
FIG. 1 is an exterior side view of a fundus photographing apparatus according to an example of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In the above apparatus, in some cases optimization control is started in an inappropriate alignment state. In such cases, the optimization control cannot be accurately performed. Further, during optimization control, an optimum alignment state may be lost by the movement of the examinee (examinee's eye), resulting in photography variation. The photography variation refers to a difference in the results of taking images of the same site under the same conditions. Furthermore, the optimization control fails in some cases. Such a failure makes a photographing operation difficult, and thus imposes a heavy burden on the examiner.

An object of the present disclosure is to provide a fundus photographing apparatus that can perform photography easily with little variations.

The fundus photographing apparatus includes: a measurement unit including an optical coherence tomography system configured to obtain a tomographic image of the fundus of an examinee's eye by detecting an interference state between measurement light from the fundus of the examinee's eye and reference light; a detection unit configured to detect an alignment state perceived as a relative positional relationship between the measurement unit and the examinee's eye; and a controller configured to perform adjustment of the optical coherence tomography system with respect to the fundus of the examinee's eye based on a detection result from the detection unit. The adjustment of the optical coherence tomography system includes at least one of an optical path length adjustment, which adjusts an optical path length difference between the measurement light and the reference light, and a focus adjustment.

This fundus photographing apparatus can easily perform photography with little variations.

In the following, an embodiment according to the present disclosure will be described with reference to the drawings. FIGS. 1 to 3 and FIGS. 4A and 4B are diagrams each illustrating the configuration of the fundus photographing apparatus according to the present embodiment. In the present embodiment, the axial direction of the examinee's eye ("eye") E corresponds to a Z direction, the horizontal direction corresponds to an X direction, and the vertical direction corresponds to a Y direction. Thus, the surface direction of the fundus corresponds to an X-Y direction.

<Outline>

Figure 2:
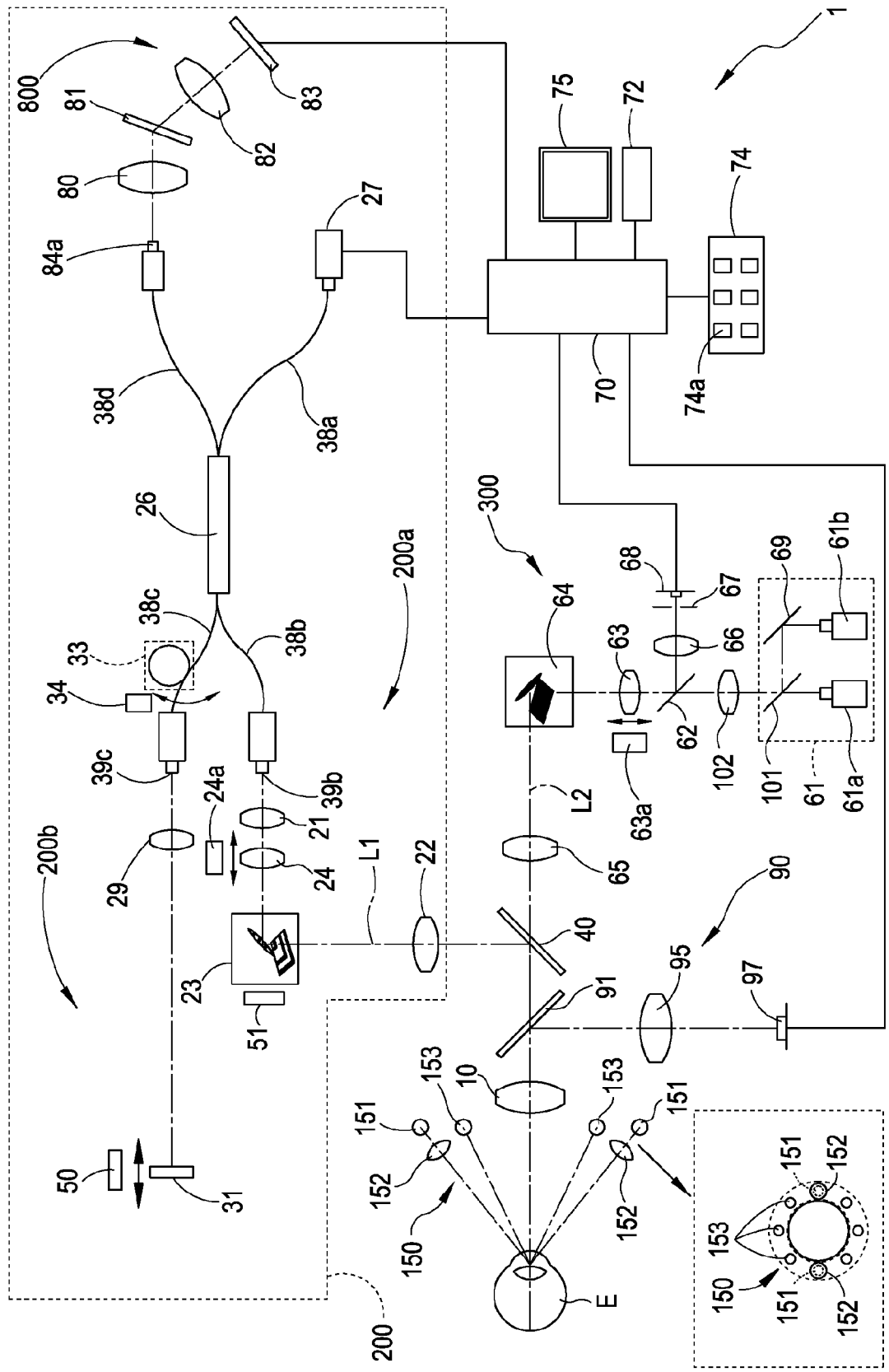
FIG. 2 is a schematic diagram illustrating an optical system and a control system housed in the body of the fundus photographing apparatus.
Figure 4A:
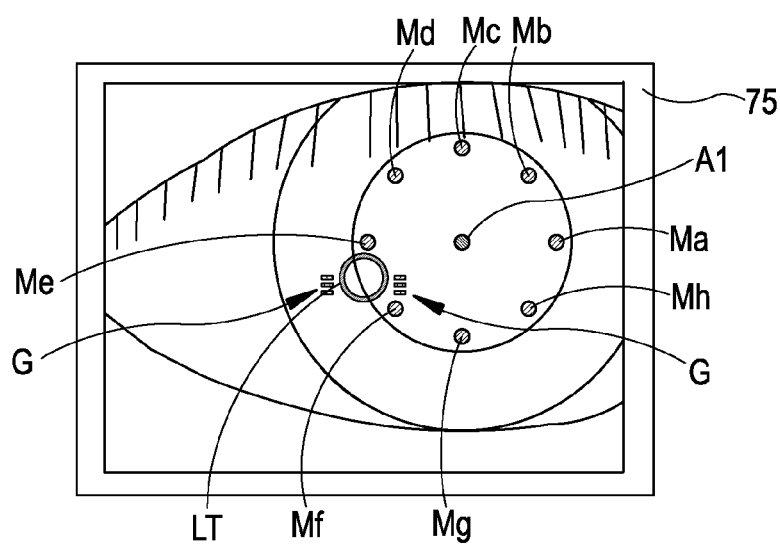
FIGS. 4A and 4B are diagrams illustrating an example of an anterior segment image displayed on a monitor.
Figure 4B:
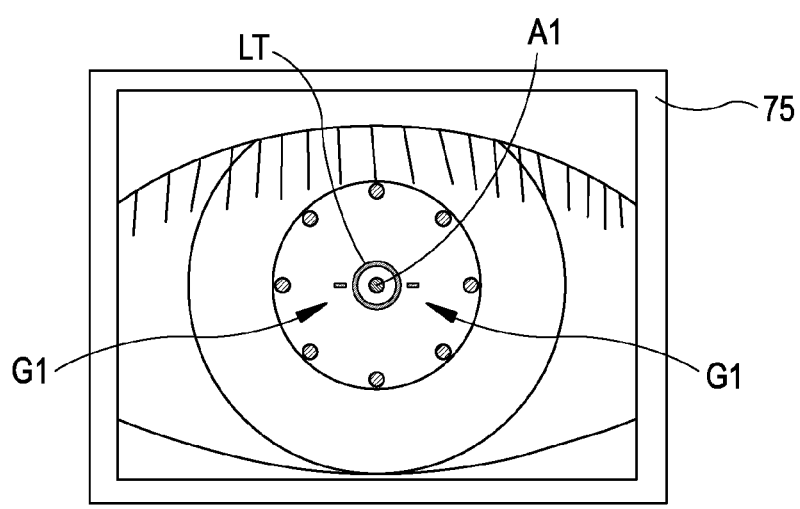

An outline of the fundus photographing apparatus according to the present embodiment will be described. As illustrated in FIG. 2, the fundus photographing apparatus (optical coherence tomography device) 1 according to the present embodiment includes an anterior segment imaging optical system (anterior segment observing optical system) 90, an alignment target projection optical system 150, an optical coherence tomography system (OCT system) 200, an observing optical system 300, and a control means (controller (CPU)) 70. These optical systems are housed in a measurement unit (apparatus body) 3.

The optical coherence tomography system 200 obtains a tomographic image of an object by using OCT principles. Thus, the optical coherence tomography system 200 includes, for example, an interferometer with a measurement optical path and a reference optical path. The optical coherence tomography system 200 includes a light source 27, a splitter (light splitter), the measurement optical path, the reference optical path, a combiner (optical combiner), and a light detector (hereafter, detector) 83. The splitter splits light from the light source into two paths, the measurement optical path and the reference optical path. The optical scanner 23 is disposed in the measurement optical path. The optical scanner 23 scans the fundus with the light from the light source 27. As the splitter or the combiner, for example, a beam splitter, a half mirror, a fiber coupler, or a circulator may be used. The measurement optical path guides the light toward the fundus. The reference optical path causes the light (reference light) from the light source 27 to propagate in the apparatus. The reference optical path also causes the reference light and the measurement light to interfere with each other. The combiner combines fundus-reflected light with the reference light from the reference optical path. Here, the fundus-reflected light is obtained when the measurement light from the measurement optical path is reflected by the fundus. In other words, the fundus-reflected light and the reference light interfere with each other at the combiner, and thus interference signal light (interference light) is obtained. Then, the interference light is received by the detector 83.

The controller 70 processes an output signal from the detector 83 to obtain depth information (an A scan signal). When a tomographic image of the fundus is obtained, the controller (arithmetic and control unit) 70 controls the optical scanner 23 to scan the eye with the measurement light in a transverse direction. Thus, the controller 70 obtains depth information corresponding to each scanned position. The controller 70 arranges a series of the depth information corresponding to the respective scanned positions in the scan direction. Thus, a tomographic image of the fundus is obtained.

The OCT may be spectral-domain OCT (SD-OCT), swept-source OCT (SS-OCT), or TD-OCT.

The present apparatus also includes an alignment adjuster (alignment adjustment means) configured to adjust the relative positional relationship between the apparatus body 3 and the examinee's eye. The alignment adjuster according to the present embodiment may be a driving part (XYZ driving part) 6. The driving part (XYZ driving part) 6 causes relative movement of the apparatus body 3 in a left-right direction, an up-down direction (Y direction), and a front-rear direction with respect to the examinee's eye E. The alignment adjuster may be a driving part that moves a face support unit 5 that supports the examinee's face with respect to the apparatus body 3.

The present apparatus also includes an optical member (reference mirror) 31, a focusing optical member (focusing lens) 24, an optical path length adjuster (optical path length adjustment means), and a focus adjuster (focus adjustment means). The optical member 31 is disposed in the optical path of the measurement light or the reference light. The optical path length adjuster adjusts the optical path length of the reference light by driving the optical member 31 such that the fundus tomographic image can be obtained. The focus adjuster moves the focusing optical member 24 to a focus position with respect to the fundus of the examinee's eye. Thus, the focus adjuster performs focus adjustment with respect to the fundus of the examinee's eye.

The OCT system 200 includes the optical scanner (scanning unit) 23 and the detector 83. The optical scanner (scanning unit) 23 scans the fundus two-dimensionally with the light emitted from the light source 27. The detector 83 detects an interference state of the interference light. The OCT system 200 is used to obtain a tomographic image of the fundus of the examinee's eye on the basis of a detection signal from the detector 83.

The observing optical system 300 includes an irradiation optical system that irradiates the fundus of an examinee's eye with illuminating light, and a light receiving optical system. The light receiving optical system includes a light receiving device 68 that receives the fundus-reflected light. The observing optical system 300 (or the controller 70) obtains a front fundus image of the examinee's eye on the basis of an output signal from the light receiving device 68. The light receiving device 68 may be a scanning laser ophthalmoscope (SLO) or a fundus camera.

The controller (detection unit; detection means) 70 detects the relative positional relationship (alignment state) between the apparatus body 3 and the examinee's eye E. Based on a detection result, the controller 70 starts at least one of optical path length adjustment and focus adjustment. In other words, the controller 70 performs optimization control regarding the OCT system 200. Of course, the controller 70 may conduct polarization adjustment as well as optical path length adjustment and focus adjustment during optimization control.

For example, the alignment state is detected by the anterior segment observing optical system 90. In this case, the controller 70 detects the alignment state on the basis of a photographing signal from the anterior segment observing optical system 90. For example, the face support unit 5 includes a chin rest and/or a forehead rest, each of which may be fitted with a sensor for sensing that the examinee has made contact with the chin rest or the forehead rest. Based on such sensing, the controller 70 may start optimization control. For example, the controller 70 conducts optimization control upon power-up of the apparatus body 3. In this case, a model eye may be installed in the apparatus body 3, and optimization control may be performed by using the model eye upon power-up.

For example, the alignment state is detected on the basis of the photographing signal from the anterior segment observing optical system 90. For this detection, the alignment target projection optical system 150 may be used. The alignment target projection optical system 150 projects alignment light onto the examinee's eye so as to form an alignment target in the vicinity of the cornea. In this case, the anterior segment observing optical system 90 photographs the alignment target, and the controller 70 detects the alignment state on the basis of the alignment target. The controller 70 then starts at least one of optical path length adjustment and focus adjustment on the basis of the result of alignment state detection. In other words, the controller 70 performs optimization of the OCT system 200.

In the detection of the alignment state on the basis of the photographing signal from the anterior segment observing optical system 90, for example, the pupil position may be detected from the anterior segment front image obtained by the anterior segment observing optical system 90. In this case, the relative position of the detected pupil position to the optical axis of the OCT system 200 is detected.

For example, at least one of optical path length adjustment and focus adjustment is started on the basis of whether the detection result is within a predetermined allowable range. In this case, when the detection result is within the allowable range, the controller 70 starts at least one of optical path length adjustment and focus adjustment. Thus, the controller 70 performs optimization control for the OCT system 200. In other words, when the alignment state detection result is used, the controller 70 starts optimization control on the basis of an alignment adjustment completion signal.

When optimization control is started on the basis of the alignment state detection result, optimization control may be started upon completion of the alignment adjustment in the X, Y, and Z directions.

For example, optimization control is started upon completion of the alignment adjustment in the X-Y direction. In this case, the controller 70 may conduct the alignment adjustment in the Z direction and optimization control in parallel. In other words, the controller 70 starts at least one of optical path length adjustment and focus adjustment when the detection result concerning the alignment state (relative positions of the apparatus body 3 and the examinee's eye E in the up-down and right-left directions) satisfies the alignment allowable range. The controller 70 then starts at least one of optical path length adjustment, focus adjustment, and polarization adjustment, and then starts the alignment adjustment in the Z direction. In other words, the controller 70 drives the XYZ driving part 6 on the basis of the result of detection of the relative positions of the apparatus body 3 and the examinee's eye in the front-rear direction (Z direction) (alignment state in the Z direction). Thus, the controller 70 relatively adjusts the alignment state in the front-rear direction.

During the optical path length adjustment, the position of the optical member for adjusting the optical path length in the Z direction (depth direction) may be corrected. Preferably, the correction is performed on the basis of the distance between the examinee's eye and the apparatus body 3 (eye examination distance) at the start of optimization control. For example, the controller 70 calculates the eye examination distance in the Z direction at the start of optimization control, and stores the result of calculation in a memory 72. The controller 70 calculates the eye examination distance in the Z direction upon completion of the alignment adjustment (position adjustment) in the Z direction. Then, the controller 70 calculates the difference between the eye examination distances before and after completion of the alignment adjustment in the Z direction. Based on the result of the calculation, the controller 70 corrects the position of the optical member for optical path length adjustment (such as the reference mirror 31).

<After Start of Optimization Control>

The controller 70 detects the alignment state after starting at least one of optical path length adjustment and focus adjustment. Further, the controller 70 adjusts the relative positions of the apparatus body 3 and the examinee's eye by driving the XYZ driving part 6 on the basis of the detection result. The controller 70 repeatedly performs the detection and adjustment.

For example, the controller 70 starts at least one of optical path length adjustment and focus adjustment. Thereafter, when the detection result deviates out of the allowable range, the controller 70 adjusts the alignment state by driving the XYZ driving part 6 so as to bring the detection result within the allowable range.

In the alignment state detection, the controller 70 detects a displacement (misalignment) between the detected alignment state and a correct alignment state. During focus adjustment, the controller 70 may correct the focus position information with respect to the fundus in accordance with the amount of misalignment. For example, the controller 70 obtains an evaluation value for evaluating the focus state (such as a total of image brightness value, or the number of edges) depending on the scanned position. At this time, the controller 70 detects the misalignment depending on the scanned position. The controller 70 then corrects the focus evaluation value on the basis of the result of detection of misalignment. The amount of correction of the evaluation value is set in advance experimentally or by simulation.

After completion of optimization control, the controller 70 may detect the alignment state. When the detection result is out of the allowable range, the controller 70 may perform optimization control again.

The controller 70 may use displacement information about the alignment state as an alignment state detection result.

In the fundus photographing apparatus 1, in order to adjust the difference in optical path length between the measurement light and the reference light, at least one of optical members disposed in an OCT system 100 is moved in the optical axis direction. For example, a reference optical system 110 includes a member for moving an optical member in the reference optical path. The member adjusts the optical path length difference between the measurement light and the reference light. The member (configuration) for modifying the optical path length difference may be disposed in the measurement optical path. An optical member (such as an end portion of an optical fiber) disposed in the measurement optical path may be moved in the optical axis direction.

EXAMPLE

An example of the present disclosure will be described with reference to the drawings. FIG. 1 is an exterior side view of the fundus photographing apparatus according to the present example.

The present apparatus includes a base 7, a movable table 2, an apparatus body 3, a joystick 4, a face support unit 5, and an XYZ driving part 6. The movable table 2 is movable in the left-right direction (X direction) and the front-rear (operating distance) direction (Z direction) with respect to the base 7. The apparatus body 3 is movable with respect to the movable table 2 in three-dimensional directions. The apparatus body 3 serves as a housing for housing optical systems as will be described later. The face support unit 5 is fixedly attached to the base 7 for supporting the examinee's face. The XYZ driving part 6 is mounted on the movable table 2. The XYZ driving part 6 is configured to move the apparatus body 3 in the left-right direction, the up-down direction (Y direction), and the front-rear direction relatively with respect to the examinee's eye E. By operating the joystick 4, the movable table 2 can be moved on the base 7 in the X and Z directions. By rotating a rotary knob 4a, the XYZ driving part 6 performs a Y-drive. In other words, the XYZ driving part 6 moves the apparatus body 3 in the Y direction. On the examiner side of the apparatus body 3, a monitor 75 for displaying a fundus tomographic image, an anterior segment observation image, and the like is installed.

FIG. 2 is a schematic diagram of the optical systems and control systems housed in the apparatus body 3. The optical systems include the OCT system (optical coherence tomography system) 200, the observing optical system (scanning laser ophthalmoscope (SLO) optical system) 300, the target projection optical system (projection optical system) 150, and the anterior segment observing optical system 90.

The OCT system 200 obtains a tomographic image of the eye E. The target projection optical system 150 projects an alignment target onto the eye E. The anterior segment observing optical system 90 observes a front image of an anterior segment Ea. A dichroic mirror 91 transmits the measurement light from the OCT system 200 and reflects the light irradiated from the projection optical system 150 and reflected by the anterior segment. These optical systems are built inside the apparatus body 3. The optical systems are three-dimensionally moved with respect to the eye E by an aligning movable mechanism (which may be either manual or electric) including the joystick 4 and the rotary knob 4a.

<Optical Coherence Tomography System (OCT System)>

The OCT system 200 includes a measurement optical system 200a and a reference optical system 200b. The OCT system 200 also includes a spectral optical system 800. The spectral optical system 800 disperses the interference light between the reference light and the measurement light according to frequencies (wavelengths). The dispersed interference light is received by a light receiving means (a one-dimensional light receiving device according to the present embodiment).

A dichroic mirror 40 reflects the measurement light (with λ of around 840 nm, for example) emitted from the OCT light source (measurement light source) 27 of the OCT system 200. Meanwhile, the dichroic mirror 40 transmits laser light (which is different from the light from the OCT light source 27 and has λ of around 780 nm, for example) emitted from an SLO light source 61a of the SLO optical system 300. The dichroic mirror 40 makes a measurement light axis L1 of the OCT system 200 and a measurement light axis L2 of the SLO optical system 300 coaxial.

First, the configuration of the OCT system 200 disposed on the reflected side of the dichroic mirror 40 will be described. The OCT light source 27 emits low coherency light used as the measurement light and the reference light for the OCT system 200. The OCT light source 27 is an SLD light source, for example. The light source used as the OCT light source 27 has the central wavelength of 840 nm and a band of 50 nm, for example. A fiber coupler (splitter) 26 provides the functions of both a light splitting member and a light combining member. The light emitted by the OCT light source 27 is split by the fiber coupler 26 into the reference light and the measurement light via an optical fiber 38a as a light guiding path. The measurement light travels via an optical fiber 38b toward the examinee's eye E. The reference light travels via an optical fiber 38c and a polarizer (polarization element) 33 toward the reference mirror 31.

In the optical path for outputting the measurement light toward the examinee's eye E, there are disposed an end portion 39b of the optical fiber 38b from which the measurement light is outputted, a collimator lens 21, the focusing optical member (focusing lens) 24, the scanning unit (optical scanner) 23, a reflecting mirror 25, and a relay lens 22. The scanning unit 23 includes two galvanometer mirrors. The scanning unit 23 is driven by a scan driving mechanism 51. The scanning unit 23 scans the fundus (object) with the measurement light two-dimensionally (in the X-Y direction). The scanning unit 23 may include an AOM (acoustico-optic modulator) or a resonant scanner.

The dichroic mirror 40 and the objective lens 10 have the function of a light guiding optical system for guiding the OCT measurement light from the OCT system 200 to the fundus of the examinee's eye.

The focusing lens 24 is driven by a driving mechanism 24a. The focusing lens 24 is movable in the optical axis direction and used for correcting the diopter scale with respect to the fundus of the examinee.

The measurement light output from the end portion 39b of the optical fiber 38b is collimated by the collimator lens 21. The measurement light then passes through the focusing lens 24. Thereafter, the direction in which the measurement light is reflected is changed as the two galvanometer mirrors of the scanning unit 23 are driven. The measurement light reflected by the scanning unit 23 is then reflected by the reflecting mirror 25. The measurement light further passes through the relay lens 22, is reflected by the dichroic mirror 40, and then condensed at the fundus of the examinee's eye via the objective lens 10.

Reflected light (fundus-reflected light) obtained as the measurement light is reflected by the fundus Ef passes through the objective lens 10, is reflected by the dichroic mirror 40, and then travels toward the OCT system 200. The measurement light further passes through the relay lens 22, the reflecting mirror 25, the two galvanometer mirrors of the scanning unit 23, the focusing lens 24, and the collimator lens 21 and enters the end portion 39b of the optical fiber 38b. The measurement light that has entered the end portion 39b passes through the optical fiber 38b, the fiber coupler 26, and an optical fiber 38d and reaches an end portion 84a of the optical fiber 38d.

The reference optical system 200b produces the reference light that is combined with the fundus-reflected light. The reference optical system 200b may be of a Michelson system or a Mach-Zehnder system. The reference optical system 200b may include, for example, a catoptric optical system (such as the reference mirror 31). The reference optical system 200b reflects the light from the coupler 104 by the catoptric optical system. Thus, the light is returned to the coupler 104 again and guided toward the detector 120. In another example, the reference optical system 200b may include a transmission optical system (such as an optical fiber). The transmission optical system transmits the light from the coupler 104, instead of returning it. Thus, the light is guided to the detector 120.

For example, in the optical path for outputting the reference light toward the reference mirror 31, there are disposed the optical fiber 38c, an end portion 39c of the optical fiber 38c from which the reference light is outputted, a collimator lens 29, and the reference mirror 31. A part of the optical fiber 38c constitutes the polarizer 33. For example, the polarizer 33 includes a metal housing in which a part of the optical fiber 38c is housed in coil shape. The driving mechanism 34 rotates the polarizer 33 so as to change the polarization direction of the reference light.

The polarizer 33 according to the present embodiment aligns the polarization directions of the measurement light and the reference light. Specifically, the polarizer 33 adjusts the polarization direction of at least one of the measurement light and the reference light. The polarizer 33 is disposed in at least one of the measurement optical path and the reference optical path. The polarizer 33 is not limited to the above configuration. For example, the polarizer 33 is a member that changes the polarization direction of light by adjusting the rotation angle of a ½ wavelength plate or a ¼ wavelength plate about the optical axis. The polarizer 33 may be a member that changes the polarization direction of light by deforming the fiber by applying pressure.

A reference mirror driving mechanism (second driving part) 50 drives the reference mirror 31 (second optical member) disposed in the reference optical path so as to adjust the optical path length of the measurement light or the reference light. According to the present embodiment, the reference mirror 31 is disposed in the reference optical path and movable in the optical axis direction. Thus, the reference mirror 31 can change the optical path length of the reference light.

The reference light emitted from the end portion 39c of the optical fiber 38c is made into a parallel light flux by the collimator lens 29. The reference light is reflected by the reference mirror 31, condensed by the collimator lens 29, and then enters the end portion 39c of the optical fiber 38c. The reference light that has entered the end portion 39c passes through the optical fiber 38c and the polarizer 33 and reaches the fiber coupler 26.

The reference light produced by the light emitted from the light source 27 and the fundus-reflected light obtained when the measurement light is reflected by the fundus of the examinee's eye are combine by the fiber coupler 26, thereby producing the interference light. The interference light is output from the end portion 84a via the optical fiber 38d.

The spectral optical system 800 (spectrometer unit) disperses the interference light into individual frequency components so as to obtain an interference signal for each frequency. The spectral optical system 800 includes a collimator lens 80, a grating mirror (diffraction grating) 81, a condenser lens 82, and a light receiving device (detector) 83. The light receiving device 83 includes a one-dimensional element (line sensor) having sensitivity to light of wavelengths in the infrared region.

The interference light emitted from the end portion 84a is converted into parallel light by the collimator lens 80 and then dispersed by the grating mirror 81 into frequency components. The dispersed interference light is condensed at the light receiving plane of the detector (light receiving device) 83 via the condenser lens 82. Thus, spectrum information of an interference pattern is recorded in the light receiving device 83. Based on an output signal from the light receiving device 83, the controller 70 captures a tomographic image of the eye. In other words, the spectrum information (light receiving signal) is inputted from the light receiving device 83 to the controller 70. The controller 70 measures information about the examinee's eye in the depth direction thereof by analyzing the spectrum information through Fourier transform. The controller 70 can obtain the tomographic image by scanning the fundus with the measurement light in a predetermined transverse direction by using the scanning unit 23. For example, the controller 70 can obtain a tomographic image (fundus tomographic image) of the fundus of the examinee's eye in the XZ plane or the YZ plane by scanning the fundus with the measurement light in the X direction or the Y direction (according to the present embodiment, the system by which a tomographic image is obtained by such one-dimensional scan of the fundus with the measurement light is referred to as a "B scan"). The obtained fundus tomographic image is stored in the memory 72 connected to the controller 70. The controller 70 may further drive the scanning unit 23 to scan the fundus with the measurement light two-dimensionally in the X-Y direction. Thus, the controller 70 can obtain a two-dimensional moving image of the fundus of the examinee's eye with respect to the X-Y direction, or a three-dimensional image of the fundus of the examinee's eye, on the basis of the output signal from the light receiving device 83.

<Observing Optical System (SLO Optical System)>

Next, the SLO optical system (confocal optical system) 300 disposed in the transmission direction of the dichroic mirror 40 will be described. The SLO optical system 300 is used as an observing optical system for acquiring a front image of the fundus of the examinee's eye. The SLO optical system 300 includes an illuminating optical system that illuminates the fundus of the examinee's eye, and a light receiving optical system. The light receiving optical system includes a light receiving device. The light receiving device receives reflected light from the examinee's eye illuminated by the illuminating optical system. Based on a light receiving signal output from the light receiving device, a front image of the fundus of the examinee's eye is obtained.

The light output unit 61 includes a first light source (SLO light source) 61a, a second light source (fixation light source) 61b, a mirror 69, and a dichroic mirror 101.

The SLO light source 61a is a light source that emits high coherency light. The SLO light source 61a includes a laser diode light source with λ=780 nm, for example. The fixation light source 61b emits light with a wavelength in the visible region. The fixation light source 61b includes a light source with λ=630 nm (such as a laser diode light source or a SLD light source), for example. The laser light emitted by the SLO light source 61a is transmitted through the dichroic mirror 101 and travels via a collimator lens 102 to a beam splitter 62. The visible light emitted by the fixation light source 61b is bent by the mirror 69 and then reflected by the dichroic mirror 101. Thereafter, the visible light is made coaxial with the laser light from the SLO light source 61a.

In the optical path for outputting the laser light from the SLO light source 61a toward the examinee's eye E, there are disposed the collimator lens 102, a focusing lens 63, a scanning unit 64, a relay lens 65, and the objective lens 10. The focusing lens 63 is movable in the optical axis direction in response to the refraction error of the examinee's eye. The scanning unit 64 includes a combination of a galvanometer mirror and a polygon mirror. The mirrors are driven by the scan driving mechanism 52 so that the fundus is scanned at high speed with the measurement light in the X-Y direction. The reflecting planes of the galvanometer mirror and the polygon mirror are disposed at positions substantially conjugate with the pupil of the examinee's eye.

Between the SLO light source 61a and the focusing lens 63, the beam splitter 62 is disposed. In the reflected direction of the beam splitter 62, a condenser lens 66, a confocal opening 67, and an SLO light receiving device 68 are disposed. The condenser lens 66 is included in the confocal optical system. The confocal opening 67 is disposed at a position substantially conjugate with the fundus.

The laser light (measurement light) emitted by the SLO light source 61a is transmitted through the beam splitter 62 and then reaches the scanning unit 64 via the focusing lens 63. The reflected direction of the laser light is changed by the galvanometer mirror and the polygon mirror. The laser light reflected by the scanning unit 64 is transmitted through the dichroic mirror 40 via the relay lens 65. Thereafter, the laser light is condensed at the fundus of the examinee's eye via the objective lens 10.

The laser light reflected by the fundus passes through the objective lens 10, the relay lens 65, the galvanometer mirror and polygon mirror of the scanning unit 64, and the focusing lens 63 and is then reflected by the beam splitter 62. The laser light is further condensed by the condenser lens 66, and then received by the light receiving device 68 via the confocal opening 67. The light receiving device 68 that has received the laser light outputs a light receiving signal to the controller 70. The controller 70 obtains a front image of the fundus of the examinee's eye on the basis of the light receiving signal. The obtained front image is stored in the memory 72. An SLO image is obtained by laser light scanning in a vertical direction (sub-scan) by the galvanometer mirror and by laser light scan in a horizontal direction (main scan) by the polygon mirror of the scanning unit 64.

<Alignment Target Projection Optical System>

The projection optical system 150 is used for projecting a target onto a cornea Ec. In the projection optical system 150, a plurality of near-infrared light sources is disposed. The near-infrared light sources are disposed coaxially at 45° intervals about the optical axis, as depicted within dotted lines in the upper left of FIG. 2. The projection optical system 150 includes a first target projection optical system and a second target projection optical system. The first target projection optical system (0° and 180°) has an infrared light source 151 and a collimating lens 152. These are disposed left-right symmetrically across a vertical plane passing through the optical axis L1. The second target projection optical system is disposed at a position different from the first target projection optical system. The second target projection optical system has six near-infrared light sources 153. In FIG. 2, a part of the first target projection optical system (0° and 180°) and the second target projection optical system (45° and 135°) is depicted for convenience sake. The light source 151 doubles as an anterior segment illumination. Of course, a separate light source for anterior segment illumination may be provided.

<Anterior Segment Observing Optical System>

The anterior segment observing optical system 90 is disposed to capture an anterior segment image of the eye E. The anterior segment observing optical system 90 includes the objective lens 10, the dichroic mirror 91, an image forming lens 95, and a two-dimensional imaging device (two-dimensional light receiving device) 97.

In the projection optical system 150, the light fluxes of anterior segment reflected light and alignment light are reflected by the dichroic mirror 91 via the objective lens 10. The light fluxes are then received by the two-dimensional imaging device 97 via the image forming lens 95. Thus, the two-dimensional imaging device 97 captures an anterior segment image. Data for the anterior segment image is transmitted to the controller 70. The controller 70 causes the anterior segment image to be displayed on the monitor 75 (see FIGS. 4A and B).

According to the present embodiment, the projection optical system 150 and the anterior segment observing optical system 90 are used as an alignment detecting optical system. The alignment detecting optical system guides the relative positional relationship (alignment state) between the eye E and the apparatus body 3 toward a predetermined positional relationship (state). For example, the projection optical system 150 and the anterior segment observing optical system 90 are used to guide the distance between the eye E and the apparatus body 3 (eye examination distance) to a predetermined correct operating distance.

The alignment detecting optical system is configured to detect the alignment state with respect to the Z direction (Z-alignment state). For example, the Z-alignment state is detected by projecting alignment light onto the eye E diagonally and receiving the reflected light from a diagonally opposite direction.

<Control System>

The controller 70 controls the apparatus as a whole, performs measurements, and processes the tomographic image, for example. The controller 70 is connected to the monitor 75 and controls the displayed image. To the controller 70, there are connected the memory (storage unit) 72, an operating unit 74 for performing various operations, the driving mechanisms 24a, 34, 50, 51, and 63a, the light sources 27, 61a, 61b, 151, and 153, the detector 120, the imaging device 97, the light receiving device 68, the XYZ driving part 6, the joystick 4, and the like.

The controller 70 detects the alignment state on the basis of the photographing signal output from the imaging device 97. The controller 70 outputs the detection result to the monitor 75. The controller 70 may control the XYZ driving part 6 so that the alignment detection result (such as the amount of misalignment) satisfies a predetermined allowable range. Thus, the controller 70 can cause the apparatus to be automatically moved with respect to the eye E (i.e., perform automatic alignment (automatic alignment adjustment)).

<Control Operation>

An operation of the fundus photographing apparatus with the above connection will be described. FIG. 3 is a flowchart illustrating the flow of a control operation according to the present example.

The examiner fixes the examinee's face on the face support unit 5. The examiner instructs the examinee to gaze a fixation target, which is not depicted. Then, the examiner operates the joystick 4 to move the apparatus body 3 so as to adjust the alignment state. The anterior segment is then photographed by the imaging device 204, and an anterior segment image and target images Ma to Mh are displayed on the monitor 75 (see FIGS. 4A and B).

For example, the controller 70 detects the XY coordinates at the center of a ring formed by the target images Ma to Mh as the position of a substantial apex of the cornea. The controller 70 then causes an alignment target A1 corresponding to the apex position to be electronically displayed on the monitor 75 (see FIG. 4A). According to the present example, a reticle LT is an alignment reference position that is set as the position at which the corneal apex position and the optical axis L1 of the apparatus are aligned. The reticle LT is electronically displayed on the monitor 75.

Further, the controller 70 compares the interval between the target images Ma and Me at infinity and the interval between the targets image Mh and Mf at finite points. Thus, the controller 70 determines the amount of misalignment (amount of alignment deviation) in the Z direction (see JP-A-6-46999 for more detail). Then, the controller 70 causes indicators G to be displayed on the monitor 75. The controller 70 increases or decreases the number of the indicators G on the basis of the amount of misalignment.

The controller 70 detects the alignment state on the basis of the photographing signal from the imaging device 97. In this case, the controller 70 calculates the XY coordinates at the center of the ring formed by the target images Ma to Mh detected by the imaging device 97. Thus, the controller 70 determines the alignment state in the up-down and right-left directions. When the apparatus body 3 is displaced in the operating distance direction (Z direction), the controller 70 compares the interval between the target images Ma and Me at infinity and the interval between the target images Mh and Mf at the finite points. Thus, the controller 70 determines the alignment state in the Z direction. Then, the controller 70 performs the automatic alignment (automatic alignment adjustment) by controlling the XYZ driving part 6 on the basis of the result of detection of the alignment state (see FIG. 4B).

According to the present example, the alignment state is adjusted by the automatic alignment adjustment (automatic alignment mode). However, the alignment state may be manually adjusted. In this case, the examiner operates the joystick 4 while monitoring the target A1 displayed on the monitor (display monitor) 75. In this way, the examiner adjusts the position of the apparatus body 3 in the X-Y direction so that the target A1 is within the reticle (reticle mark) LT. Thereafter, the examiner moves the apparatus body 3 to the front or rear until the indicator G shows completion of alignment adjustment. In this way, the examiner adjusts the position of the apparatus body 3 in the Z direction, whereby the alignment adjustment is completed.

<Alignment Determination>

The controller 70 determines the appropriateness of the alignment state, and starts optimization control on the basis of the determination result.

The controller 70 determines whether the amount of misalignment is within a predetermined allowable range. For example, the controller 70 determines whether the misalignment in the X, Y, and Z directions (such as the displacement between the target A1 and the reticle LT) is not more than 0.5 mm. For example, the controller 70 determines whether the amount of misalignment in the X, Y, and Z directions (XYZ deviation amount) is within an allowable range for completing the alignment adjustment. The controller 70 determines the appropriateness of the alignment state in the X, Y, and Z directions depending on the determination result. When the XYZ deviation amount is within the allowable range for completing the alignment adjustment, the controller 70 determines that the alignment state is correct. In this case, the controller 70 stops the XYZ driving part 6 and outputs an alignment adjustment completion signal.

When the XYZ deviation amount is not within the allowable range for completing the alignment adjustment, the controller 70 determines that the alignment state is not correct. In this case, the controller 70 performs the automatic alignment adjustment.

<Optimization Control>

When the alignment adjustment completion signal is outputted, the controller 70 produces a trigger signal for starting optimization control, and then starts an optimization control operation. The optimization enables observation of a fundus site of interest to the examiner with high sensitivity and at high resolution. According to the present example, the optimization (optimization control) includes optical path length adjustment, focus adjustment, and/or polarization state adjustment (polarizer adjustment). Optimization may be achieved when certain admissibility conditions for the fundus are satisfied, and the most appropriate state may not be realized.

During optimization control, the controller 70 performs tracking control such that the amount of misalignment satisfies an allowable range. The tracking control causes the apparatus body 3 to be moved to track the examinee's eye. For example, the controller 70 determines whether the XYZ deviation amount is within the allowable range for completing the alignment adjustment for a certain time continuously. The certain time is 10 frames of image processing, or 0.3 second, for example. In this way, the controller 70 determines whether the correct state of alignment in the X, Y, and Z directions is continuously present. When the XYZ deviation amount is within the allowable range for completing the alignment adjustment for the certain time continuously, the controller 70 determines that the correct state of alignment is continuously present. In this case, the controller 70 keeps the XYZ driving part 6 in a stopped state.

When the XYZ deviation amount is not within the allowable range for completing the alignment adjustment for the certain time continuously, the controller 70 determines that the correct state of alignment is not continuously present. In this case, the controller 70 drives the XYZ driving part 6 and resumes the automatic alignment adjustment. In this case, the controller 70 may continue optimization control while the XYZ driving part 6 is being driven (during the automatic alignment adjustment).

Of course, the controller 70 may stop the optimization control when the amount of misalignment deviates from the allowable range. After the optimization control is stopped, the controller 70 may resume optimization control when the amount of misalignment is brought back within the allowable range. When the automatic alignment adjustment is resumed, the controller 70 may repeat optimization control from the initial position.

During optimization control, the controller 70 sets the positions of the reference mirror 31 and the focusing lens 24 at their initial positions when initializing the present apparatus. Thereafter, the controller 70 performs a first optical path length adjustment by causing the reference mirror 31 to be moved from the set initial position in one direction at predetermined steps (the first automatic optical path length adjustment). In parallel with the first optical path length adjustment, the controller 70 also obtains focus position information with respect to the fundus of the examinee's eye on the basis of an SLO fundus image, which is obtained on the basis of the light receiving signal output from the light receiving device 68. Based on the focus position information, the controller 70 causes the focusing lens 24 to be moved to the focus position. In other words, the controller 70 performs auto-focus adjustment (focus adjustment). The focus position may be the position at which a contrast of a tomographic image that can be permitted as an observation image can be obtained. The focus position may not be the position at which the optimum focus state is obtained.

After the focus adjustment, the controller 70 causes the reference mirror 31 to be moved in the optical axis direction again. Thus, the controller 70 performs a second optical path length adjustment, which is readjustment of the optical path length (fine-adjustment of the optical path length). After completion of the second optical path length adjustment, the controller 70 drives the polarizer 33 to adjust the polarization state of the reference light. In this way, the controller 70 adjusts the polarization state of the measurement light (see JP-A-2012-56292 for more detail).

As described above, optimization control is completed, whereby the examiner can observe the fundus site of interest with high sensitivity and at high resolution. The controller 70 then scans the fundus with the measurement light by controlling the scanning unit 23. The controller 70 obtains a light receiving signal corresponding to the predetermined scan region from the light receiving signal (spectrum data) output from the light receiving device 83 during the scan. Based on the light receiving signal, the controller 70 forms a fundus image.

The controller 70 processes the spectrum data output from the light receiving device 83. By this process, the controller 70 forms a fundus tomographic image and a fundus front image. The fundus tomographic image and the fundus front image may be obtained simultaneously, alternately, or successively. In other words, the spectrum data is used for acquiring at least one of the fundus tomographic image and the fundus front image. The obtained fundus tomographic image and fundus front image are displayed on the monitor 75.

When a photographing switch (not shown) is operated by the examiner at a desired position, the images displayed on the monitor 75 are stored in the memory 72 as still images.

As described above, the fundus photographing apparatus 1 can perform optimization control in a correct alignment state. Thus, the fundus photographing apparatus 1 can perform optimization control accurately. Accordingly, photography variations can be easily suppressed when performing photography. Further, the probability of successful optimization control is increased, whereby the burden on the examiner can be decreased. Further, optimization control can be smoothly performed together with alignment adjustment. Thus, the examiner can easily complete preparations before photographing.

<Modifications>

In the fundus photographing apparatus 1, the controller 70 may determine whether to perform optimization control or not depending on whether optimization control has already been performed. For example, the controller 70 determines whether optimization control has already been performed prior to starting optimization control. When optimization control has already been completed, the controller 70 may not perform optimization control. The determination as to whether optimization control has been performed may include a determination as to whether a predetermined time has elapsed since the previous optimization control. The determination may include a determination as to whether data about the examinee (such as his or her patient ID) has been modified. Further, this determination may include a determination as to whether a photographing parameter (such as the scan length, photographed site, or scan pattern) has been modified.

The controller 70 may determine whether to perform optimization control or not depending on whether optimization control has already been performed after optimization control had been performed several times.

In the fundus photographing apparatus 1, blinking of the examinee's eye may be detected. The controller 70 may determine whether the alignment state is correct or not by taking the blinking into consideration. In this case, for example, the controller 70 may determine that the alignment state is correct when the alignment state cannot be detected due to the blinking. In other words, blinking may not be used for the determination. Blinking may be detected on the basis of a disappearance time of the alignment target.

The fundus photographing apparatus 1 may include a member for modifying the alignment position on the pupil so that an opaque portion of the examinee's eye can be avoided and/or the photographed site (macula photography or optic disc photography) can be modified. In this case, the examiner selects a predetermined position in the anterior segment image by using a mouse and the like (not shown) on an alignment position setting screen and the like, while observing the monitor 75, for example. The controller 70 calculates the amount of shift in the X-Y direction from an alignment reference position, which is pre-set as the position at which the corneal apex position and the optical axis L1 of the apparatus are aligned, to the coordinates position of the alignment position. Then, the controller 70 offsets the amount of deviation (amount of misalignment) between the alignment reference position and the corneal apex position so that the amount of shift ΔP can be subtracted. Thereafter, the controller 70 detects the amount of misalignment Δd. Based on the amount of misalignment Δd, the controller 70 performs the automatic alignment adjustment with respect to the eye E. Of course, the selection of the alignment position by the examiner is not a requirement. The alignment position may be set in advance depending on the photographed site and the like, and then stored in the memory 72.

The controller 70 may control the display on the display monitor 9 so that the measurement light axis L1 is moved to the alignment position set as described above. Thus, the controller 70 can guide the manual alignment operation by the examiner using the joystick (operating unit) 4. Further, the controller 70 can perform alignment adjustment depending on the measurement point. In the following, a specific technique will be described. For example, the controller 70 changes the display position of the reticle LT as the reference for the manual alignment adjustment in response to a change in the alignment position. In this way, the controller 70 guides the manual alignment operation by the examiner.

This control may not include changing the position of the reticle LT as the reference for alignment adjustment depending on the alignment position. This control may include offsetting the display position of the alignment target depending on the change in the position (alignment position) of the measurement light axis L1. In this case, the amount of deviation between the measurement point at the cornea of the examinee's eye and the measurement light axis L1 may be expressed. The display position of the alignment target may be controlled with respect to the reticle LT fixedly displayed to be the reference for manual alignment adjustment.

The fundus photographing apparatus 1 may include a comparing member. The comparing member (such as the controller 70) compares a past alignment state and the alignment state at the time of photography. For example, the controller 70 stores the date/time of photography, an anterior segment image, and the alignment position in the memory 72. The controller 70 then calls the anterior segment image and alignment position at the time of the past photography from the memory 72 when photographing.

For example, the controller 70 controls the current alignment position to correspond to the alignment position at the past photography by using the XYZ driving part 6. Thereafter, the controller 70 starts optimization control.

For example, the controller 70 performs a position matching process (such as a template matching process) for the anterior segment image (current anterior segment image) obtained at the time of alignment adjustment and the past anterior segment image. By this process, the controller 70 adjusts the current alignment position to correspond to the past alignment position. Thereafter, the controller 70 starts optimization control. Thus, photography can be performed under a photographing condition similar to the past photographing condition, whereby a follow-up can be conducted more easily. Further, images taken of the same examinee's eye can be compared more easily.

The controller 70 may conduct biometric authentication when calling up the past anterior segment image for the same patient. For example, the controller 70 detects a pattern at the iris portion from the current anterior segment image. Then, the controller 70 selects from the past anterior segment images stored in the memory 72 an anterior segment image with similar iris information.

The comparison of images may not include the above matching processes. The controller 70 may store the direction of displacement and the amount of deviation at a feature point on the anterior segment, such as the corneal apex or the pupil center, in both images and store such information in the memory 72. Then, during alignment adjustment, the controller 70 may control the XYZ driving part 6 so that the displacement direction and the amount of deviation are the same as those in the past photography.

According to the present example, the alignment adjustment in the Z direction is performed by projecting a target onto the cornea. However, the controller 70 may detect the alignment state of the apparatus body 3 with respect to the examinee's eye E in the Z direction on the basis of the A scan signal that is obtained. Based on the detection result, the controller 70 may control the XYZ driving part 6 to move the apparatus body 3 in the front-rear direction. Thus, the alignment adjustment in the Z direction can be performed automatically by using the interference signal. The controller 70 may conduct rough alignment guidance by using an alignment target projected onto the cornea. Thereafter, the controller 70 may conduct precise alignment guidance by using the interference signal.

The controller 70 may continue the automatic alignment adjustment using the interference signal even after completion of alignment adjustment. For example, after completion of alignment adjustment, when the detected position of the cornea interference signal is displaced from a predetermined alignment condition, the controller 70 controls the XYZ driving part 6 again to move the apparatus body 3.

The controller 70 may detect the alignment state in the X-Y direction from the light spot of alignment light spot as described above. Based on the detection result, the controller 70 may control the XYZ driving part 6. Thus, the controller 70 may perform the alignment adjustment in the Z direction using the interference signal and the XY alignment adjustment using the anterior segment image in parallel. During the XY alignment adjustment, the controller 70 may extract a feature site in the anterior segment image (such as the pupil center) by image processing. The controller 70 may detect the alignment state on the basis of the position information about the feature site.

The OCT system 100 may double as a projection optical system for project an alignment target onto the cornea Ec. For example, in a state in which the measurement light scan is stopped, the cornea reflection of the measurement light could be the alignment center raster. The electronic alignment target A1 may be displayed on the monitor 75 upon completion of alignment adjustment.

The alignment display electronically displayed on the display monitor 9 may be controlled to move the measurement light axis L1 to each of the alignment positions set as described above so that the manual alignment operation by the examiner can be guided and the alignment adjustment to the measurement unit 4 and each measurement point can be made. In the following, a specific technique will be described. For example, the controller 70 varies the displayed position of the reticle as the reference for manual alignment in response to a change in the alignment position, so that the examiner's manual alignment operation can be guided.

Of course, the changing of the position of the reticle LT as the reference for alignment depending on the alignment position is merely an example. The displayed position of the alignment target may be offset in response to a change in the alignment position for positioning the measurement light axis L1. In this case, the displayed position of the alignment target may be controlled with respect to the reticle LT fixedly displayed as the reference for manual alignment so that the amount of deviation between each measurement point on the examinee's eye cornea and the measurement light axis L1 can be expressed.

The present example may be configured to compare a past alignment state and the alignment state at the time of photography. For example, an image taken at a different date or time is stored in the memory 72 together with the anterior segment image and the alignment position. When photography is performed, the anterior segment image and alignment position at the time of the past photography are called from the memory 72.

The controller 70 controls the driving of the driving part 6 so that the alignment position with respect to the past anterior segment image and the alignment position with respect to the anterior segment image that is currently obtained are at the same position. When the alignment to the past alignment position is completed, the controller 70 starts optimization control.

The controller 70 performs position aligning process (such as a template matching process) between the anterior segment image that is currently being aligned and the past anterior segment image, and starts optimization control when the alignment to the past alignment position is completed. Thus, photography can be performed under a photographing condition similar to the past photographing condition, whereby a follow-up can be more easily conducted. Further, images taken of the same examinee's eye can be more easily compared.

The fundus photographing apparatus according to the present disclosure may be the first to twelfth fundus photographing apparatuses described below. A first fundus photographing apparatus includes: a measurement unit including an optical coherence tomography system for acquiring a tomographic image of the fundus of an examinee's eye by detecting an interference state between measurement light from the fundus of the examinee's eye and reference light; a detection unit that detects relative positions of the measurement unit and the examinee's eye; and a controller that performs adjustment of the optical coherence tomography system with respect to the fundus of the examinee's eye by starting at least one of an optical path length adjustment, which is responsible for driving an optical member disposed in the optical coherence tomography system for adjusting an optical path length difference between the measurement light and the reference light so that the fundus tomographic image can be obtained, and a focus adjustment, which is responsible for driving a focusing optical member disposed in the optical coherence tomography system to a focus position with respect to the fundus of the examinee's eye, based on a detection result from the detection unit.

A second fundus photographing apparatus is based on the first fundus photographing apparatus that includes an adjuster that relatively adjusts the positional relationship between the measurement unit and the examinee's eye, wherein the controller, after starting at least one of the optical path length adjustment and the focus adjustment, adjusts the relative positional relationship between the measurement unit and the examinee's eye by controlling the driving of the adjuster on the basis of the detection result detected by the detection unit.

A third fundus photographing apparatus is based on the first or the second fundus photographing apparatus that includes an anterior segment imaging/photographing optical system including an imaging device (97) for imaging or capturing an anterior segment front image of the examinee's eye, wherein the detection means detects a relative position of the measurement unit with respect to the examinee's eye on the basis of a photographing signal from the imaging device.

A fourth fundus photographing apparatus is based on the third fundus photographing apparatus that further includes an alignment target projection optical system that projects alignment light onto the examinee's eye to form an alignment target in the vicinity of the cornea, wherein the detection means detects an alignment state on the basis of the alignment target photographed by the anterior segment imaging optical system, and the control means starts at least one of the optical path length adjustment and the focus adjustment on the basis of the detection result from the detection means so as to perform adjustment of the optical coherence tomography system with respect to the fundus of the examinee's eye.

A fifth fundus photographing apparatus is based on the third fundus photographing apparatus, wherein the detection unit detects the pupil position from the anterior segment front image imaged or captured by the anterior segment imaging system, and detects the relative position of the measurement unit with respect the examinee's eye on the basis of the detected pupil position.

A sixth fundus photographing apparatus is based on any one of the first to the fifth fundus photographing apparatuses, wherein the control means starts at least one of the optical path length adjustment and the focus when the detection result detected by the detection means is within an allowable range, and performs adjustment of the optical coherence tomography system with respect to the fundus of the examinee's eye.

A seventh fundus photographing apparatus is based on any one of the first to the sixth fundus photographing apparatuses, wherein, when the detection result detected by the detection means deviates from the allowable range, the control means controls the driving of the adjustment means to bring the detection result within the allowable range.

An eighth fundus photographing apparatus is based on the sixth fundus photographing apparatus, wherein the adjustment means includes a driving part that moves the measurement unit in up-down and right-left directions and a front-rear direction with respect to the examinee's eye, and wherein the control means, when the detection result detected by the detection means deviates from the allowable range, controls the driving of the driving part to bring the detection result within the allowable range.

A ninth fundus photographing apparatus is based on the first fundus photographing apparatus that includes an adjustment means that relatively adjusts the positional relationship between the measurement unit and the examinee's eye, wherein, when the detection result of the relative positions between the measurement unit and the examinee's eye in up-down and right-left directions by the detection means satisfies an allowable range, the control means starts at least one of the optical path length adjustment and the focus adjustment, and, in parallel with at least one of the optical path length adjustment, the focus adjustment, or polarization adjustment, controls the driving of the adjustment means on the basis of the detection result of the relative positions of the measurement unit and the examinee's eye in a front-rear direction by the detection means so as to relatively adjusts the positional relationship of the measurement unit and the examinee's eye in the front-rear direction.

A tenth fundus photographing apparatus is based on any one of the first to the ninth fundus photographing apparatuses, wherein the detection unit, on an anterior segment front image imaged or captured by the anterior segment imaging system, changes an alignment reference position on the basis of an operation signal from an operating unit, and detects the relative position of the measurement unit with respect to the examinee's eye on the basis of the changed alignment reference position.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A fundus photographing apparatus comprising:
   a measurement unit comprising a housing and an optical coherence tomography system within the housing configured to obtain a tomographic image of the fundus of an examinee's eye by detecting an interference state between measurement light from the fundus of the examinee's eye and reference light;
   a detection unit configured to detect an alignment state perceived as a relative positional relationship between the measurement unit and the examinee's eye;
   a controller configured to perform adjustment of the optical coherence tomography system with respect to the fundus of the examinee's eye based on a detection result from the detection unit; and
   an alignment adjuster comprising a driving part configured to move the housing of the measurement unit, wherein
   the adjustment of the optical coherence tomography system includes at least one of an optical path length adjustment, which adjusts an optical path length difference between the measurement light and the reference light, and a focus adjustment; and
   during the optical path length adjustment or the focus adjustment, the driving part of the alignment adjuster is configured to move the housing of the measurement unit based on the detected alignment state to bring the alignment state within a predetermined range.

2. The fundus photographing apparatus according to claim 1, wherein
   the controller, after starting the adjustment of the optical coherence tomography system, adjusts the alignment state by controlling the alignment adjuster based on the detection result from the detection unit.

3. The fundus photographing apparatus according to claim 1, wherein the measurement unit further comprises within the housing an anterior segment imaging system including an imaging device configured to capture an anterior segment front image of the examinee's eye, wherein
   the detection unit detects the alignment state based on a photographing signal from the imaging device.

4. The fundus photographing apparatus according to claim 3, wherein the measurement unit further comprises within the housing an alignment target projection optical system configured to form an alignment target in the vicinity of the cornea of the examinee's eye, wherein
   the detection unit detects the alignment state based on the alignment target photographed by the anterior segment imaging system, and
   the controller starts the adjustment of the optical coherence tomography system based on the detection result from the detection unit.

5. The fundus photographing apparatus according to claim 3, wherein
   the detection unit detects the pupil position from the anterior segment front image captured by the anterior segment imaging system, and detects the alignment state based on the detected pupil position.

6. The fundus photographing apparatus according to claim 1, wherein
   the controller starts the adjustment of the optical coherence tomography system when the detection result from the detection unit is within an allowable range.

7. The fundus photographing apparatus according to claim 1, wherein
   when the detection result from the detection unit is outside an allowable range, the controller controls the alignment adjuster to bring the detection result within the allowable range.

8. The fundus photographing apparatus according to claim 7, wherein
   the driving part is configured to move the housing of the measurement unit in up-down and right-left directions with respect to the examinee's eye; and
   when the detection result from the detection unit is outside the allowable range, the controller controls the driving part to bring the detection result within the allowable range.

9. The fundus photographing apparatus according to claim 7, wherein
   when the detection result from the detection unit is within the allowable range, the controller starts the adjustment of the optical coherence tomography system; and
   when the detection result from the detection unit is outside the allowable range after the adjustment of the optical coherence tomography system is started, the controller controls the alignment adjuster to bring the detection result within the allowable range.

10. The fundus photographing apparatus according to claim 1, wherein
when the alignment state in the up-down and right-left directions is within the allowable range, the controller starts the adjustment of the optical coherence tomography system; and
the controller adjusts the alignment state in the front-rear direction by controlling the alignment adjuster based on the detection result from the detection unit in parallel with the adjustment of the optical coherence tomography system.

11. The fundus photographing apparatus according to claim 1, further comprising an operating unit configured to receive an external input, wherein
the detection unit detects the alignment state based on an alignment reference position inputted via the operating unit.

12. The fundus photographing apparatus according to claim 1, wherein
the optical path length adjustment includes driving an optical member disposed in the optical coherence tomography system to obtain the fundus tomographic image; and
the focus adjustment includes moving a focusing optical member disposed in the optical coherence tomography system to a focus position with respect to the fundus of the examinee's eye.

13. The fundus photographing apparatus according to claim 1, wherein
the measurement unit further comprises within the housing an anterior segment imaging optical system, an alignment target projection optical system, a reference mirror, a focusing lens, an optical path length adjuster, and a focus adjuster.

14. The fundus photographing apparatus according to claim 1, wherein
the driving part of the alignment adjuster is configured to move the housing of the measurement unit in up-down and right-left directions with respect to the examinee's eye.

15. The fundus photographing apparatus according to claim 1, wherein
the measurement unit further comprises within the housing an anterior segment imaging optical system, an alignment target projection optical system, a reference mirror, a focusing lens, an optical path length adjuster; and
during the optical path length adjustment or the focus adjustment, the driving part of the alignment adjuster is configured to move the housing of the measurement unit based on the detected alignment state to bring the alignment state within a predetermined range.

16. The fundus photographing apparatus according to claim 1, further comprising a base, wherein
the housing of the measurement unit is located on the base;
the measurement unit further comprises within the housing an anterior segment imaging optical system, an alignment target projection optical system, a reference mirror, a focusing lens, an optical path length adjuster; and
during the optical path length adjustment or the focus adjustment, the driving part of the alignment adjuster is configured to move the housing of the measurement unit based on the detected alignment state to bring the alignment state within a predetermined range.

17. The fundus photographing apparatus according to claim 1, wherein
the driving part of the alignment adjuster is configured to track the examinee's eye such that the driving part of the alignment adjuster moves the housing of the measurement unit to bring the alignment state within a predetermined range for a predetermined time period.

18. The fundus photographing apparatus according to claim 1, wherein
the controller is configured to output an alignment adjustment completion signal when the alignment state is within the predetermined range; and
after the controller outputs the alignment adjustment completion signal, the driving part of the alignment adjuster is configured to track the examinee's eye such that the driving part of the alignment adjuster moves the housing of the measurement unit to bring the alignment state within a predetermined range for a predetermined time period.

19. The fundus photographing apparatus according to claim 1, wherein
the controller is configured to output an alignment adjustment completion signal and stop the driving part when the alignment state is within the predetermined range;
after the controller outputs the alignment adjustment completion signal, the controller is configured to determine whether the alignment state is within the predetermined range for a predetermined time period;
when the alignment state is within the predetermined range for the predetermined time period, the controller is configured to keep the driving part in a stopped state; and
when the alignment state is not within the predetermined range for the predetermined time period, the controller is configured to resume controlling the driving part of the alignment adjuster so that driving part moves the housing of the measurement unit based on the detected alignment state to bring the alignment state within a predetermined range.

20. The fundus photographing apparatus according to claim 1, wherein
the controller is configured to output an alignment adjustment completion signal and stop the driving part when the alignment state is within the predetermined range;
during the optical path length adjustment and after the controller outputs the alignment adjustment completion signal, the controller is configured to determine whether the alignment state is within the predetermined range for a predetermined time period;
during the optical path length adjustment and when the alignment state is within the predetermined range for the predetermined time period, the controller is configured to keep the driving part in a stopped state; and
during the optical path length adjustment and when the alignment state is not within the predetermined range for the predetermined time period, the controller is configured to resume controlling the driving part of the alignment adjuster so that driving part moves the housing of the measurement unit based on the detected alignment state to bring the alignment state within a predetermined range.

* * * * *